Figure 1:
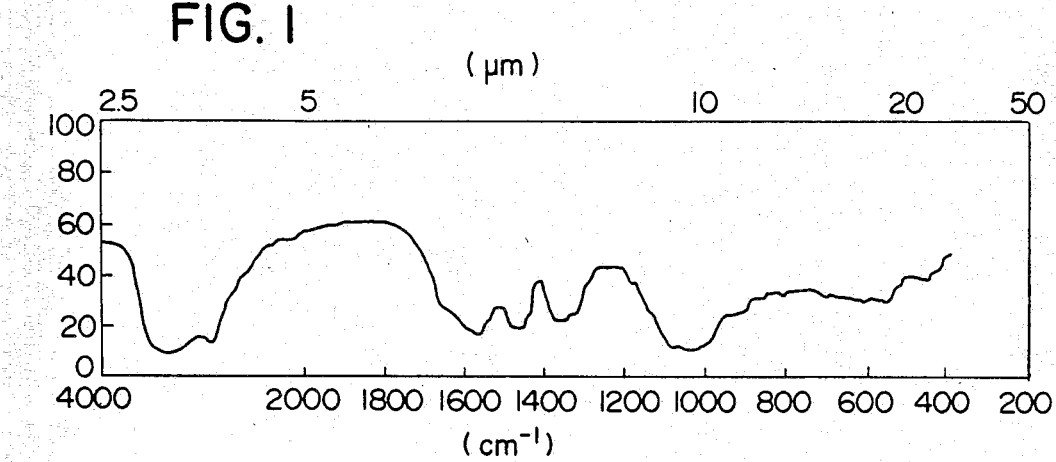

United States Patent [19]

Iwasaki et al.

[11] Patent Number: 4,515,942
[45] Date of Patent: May 7, 1985

[54] ANTIBIOTICS KA-6606 XII, XIII, XV, XVI AND XVII

[75] Inventors: Akio Iwasaki, Kawasaki; Takeo Deushi, Higashimurayama; Isamu Watanabe, Higashimurayama; Toshihito Mori, Higashimurayama, all of Japan

[73] Assignee: Kowa Company, Ltd., Aichi, Japan

[21] Appl. No.: 541,291

[22] Filed: Oct. 11, 1983

Related U.S. Application Data

[62] Division of Ser. No. 281,898, Jul. 9, 1981, Pat. No. 4,425,430.

[30] Foreign Application Priority Data

Jul. 15, 1980 [JP] Japan .................................. 55-95602
Dec. 27, 1980 [JP] Japan ............................... 55-185087

[51] Int. Cl.³ ...................... C07H 15/22; C12P 19/48
[52] U.S. Cl. .................................... 536/16.8; 435/80; 536/16.1; 536/16.6
[58] Field of Search .............................. 536/16.8, 16.1

[56] References Cited

U.S. PATENT DOCUMENTS 4,206,206 6/1980 Mori et al. .......................... 536/16.8
4,283,529 8/1981 Rosenbrook, Jr. ................. 536/16.8
4,296,106 10/1981 Umezawa et al. ................. 536/16.8
4,312,858 1/1982 Deushi et al. ...................... 536/16.8

*Primary Examiner*—Johnnie R. Brown
*Attorney, Agent, or Firm*—Wenderoth, Lind & Ponack

[57] ABSTRACT

A process for producing an antibiotic, which comprises cultivating an antibiotic KA-6606-producing strain of the genus Saccharopolyspora in a nutrient culture medium, isolating an antibiotic KA-6606-containing substance from the culture broth, and separating from the resulting antibiotic KA-6606-containing substance at least one antibiotic selected from the group consisting of antibiotic KA-6606 VII, KA-6606 VIII, KA-6606 IX, KA-6606 X, KA-6606 XI, KA-6606 XII, KA-6606 XIII, KA-6606 XIV, KA-6606 XV, KA-6606 XVI and KA-6606 XVII; and novel antibiotics KA-6606 XII, XIII and XV to XVII.

1 Claim, 11 Drawing Figures

ANTIBIOTICS KA-6606 XII, XIII, XV, XVI AND XVII

This application is a division of Ser. No. 281,898 filed July 9, 1981 now U.S. Pat. No. 4,425,430.

This invention relates to a novel process for producing antibiotics, including novel antibiotics, and to the novel antibiotics.

More specifically, this invention pertains to a process for producing antibiotics, which comprises cultivating an antibiotic KA-6606-producing strain of the genus Saccharopolyspora in a nutrient culture medium, isolating an antibiotic KA-6606-containing substance from the culture broth, and separating from the resulting antibiotic KA-6606-containing substance at least one antibiotic selected from the group consisting of antibiotics KA-6606 VII, KA-6606 VIII, KA-6606 IX, KA-6606 X, KA-6606 XI, KA-6606 XII, KA-6606 XIII, KA-6606 XIV, KA-6606 XV, KA-6606 XVI and KA-6606 XVII.

The antibiotics KA-6606 VII to KA-6606 XVII which can be produced by the process of this invention have the following structures.

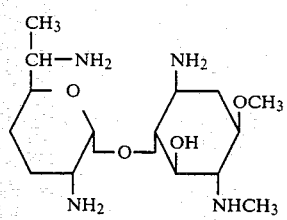

KA-6606 VII

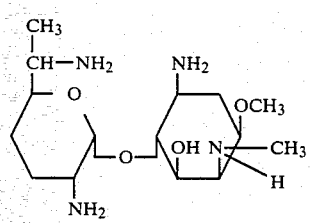

KA-6606 VIII

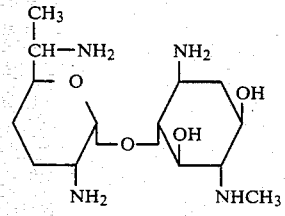

KA-6606 IX

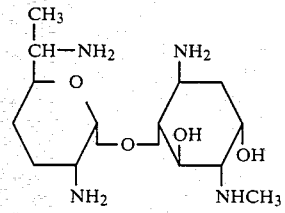

KA-6606 X

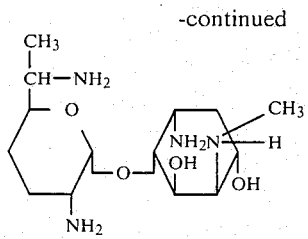

KA-6606 XI

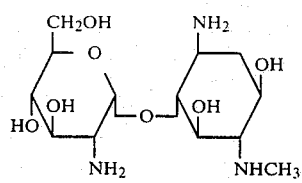

KA-6606 XII

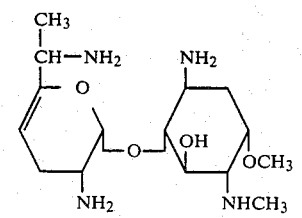

KA-6606 XIII

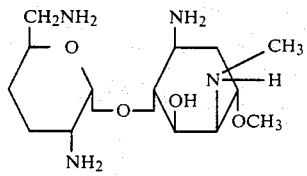

KA-6606 XIV

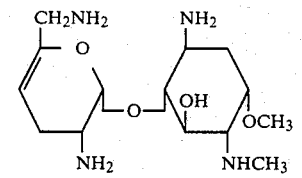

KA-6606 XV

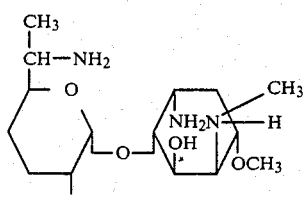

KA-6606 XVI

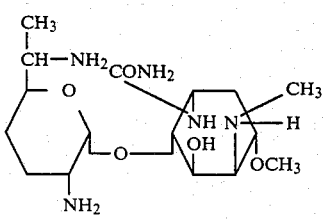

KA-6606 XVII

U.S. Pat. No. 4,206,206, corresponding to British Pat. No. 1,579,312, discloses a process for producing an antibiotic which comprises cultivating an antibiotic KA-6606-producing strain of the genus Saccharopolyspora, isolating the antibiotic KA-6606 from the culture broth, and separating at least one of antibiotics KA-6606 I, KA-6606 II, KA-6606 III and KA-6606 IV from the resulting antibiotic KA-6606.

U.S. Pat. No. 4,255,421 discloses a process for producing an antibiotic of the formula

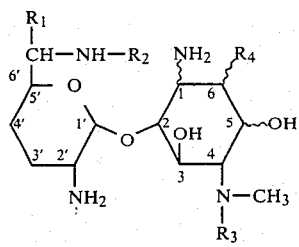

wherein $R_1$ and $R_2$ are identical or different, and each represents a hydrogen atom or a methyl group, $R_3$ represents a hydrogen atom, or an aminoacyl group having 2 to 4 carbon atoms in the acyl moiety, said aminoacyl group being optionally substituted, and $R_4$ represents a hydrogen atom or a hydroxyl group, or an acid addition salt thereof, which comprises treating a compound of the formula

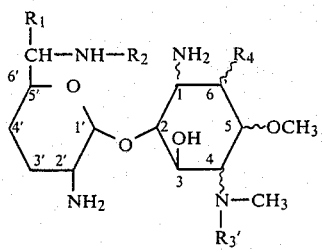

wherein $R_1$, $R_2$ and $R_4$ are as defined above, and $R_3'$ represents a moiety selected from the group consisting of a hydrogen atom, $-COCH_2NH_2$, $-COCH_2NH-CONH_2$ and $-COCH_3NHCHO$, with a strong acid, and when a compound of formula (I) wherein $R_3$ is a hydrogen atom is obtained, protecting the amino groups at the 1- and 2'-positions or the amino or methylamino group at the 6'-position of the resulting compound, then acylating it with an optionally substituted amino acid having 2 to 4 carbon atoms in the acyl moiety and a protected amino group, or a reactive derivative thereof, and then splitting off the protective group, and if desired, converting the product to an acid addition salt.

It has now been found that the antibiotics KA-6606 IX to KA-6606 XI, which can be produced from the compound of the formula (II) in the above U.S. Pat. No. 4,255,421 by a chemical process, and the aforesaid novel antibiotics KA-6606 XII, XIII and KA-6606 XV to XVII, which are not described in the literature, can be produced by using an antibiotic KA-6606-producing strain of the genus Saccharopolyspora, and separated from each other.

It has previously been unknown that the antibiotic KA-6606-containing substance produced by the above microorganism strain further includes antibiotics KA-6606 VII to KA-6606 XVII. These antibiotics KA-6606 VII to KA-6606 XVII can be isolated and recovered.

It is an object of this invention therefore to provide a fermentative process for producing antibiotics KA-6606 VII to KA-6606 XVII and the novel antibiotics included in them.

The above and other objects and advantages of this invention will become more apparent from the following description.

According to the process of the invention, a known antibiotic KA-6606-producing strain of the genus Saccharopolyspora is cultivated in a nutrient culture medium. The cultivation results in formation of the antibiotic KA-6606-containing substance containing antibiotics KA-6606 I, KA-6606 II, KA-6606 III, and KA-6606 IV which are known from the above-cited U.S. Pat. No. 4,206,206, antibiotics KA-6606 V and KA-6606 VI which, are known from Japanese Laid-Open Patent Publication No. 111497/1980, and known antibiotics KA-6606 IX, KA-6606 X and KA-6606 XI which are encompassed within the general formula of the desired antibiotics that can be obtained by the chemical process of the above-cited U.S. Pat. No. 4,255,421, and the novel antibiotics KA-6606 XII, KA-6606 XIII, KA-6606 XV, KA-6606 XVI and KA-6606 XVII. This and the above substance can be isolated.

The antibiotic KA-6606-producing strain utilized for the formation of the antibiotic KA-6606-containing substance is known, and described, for example, in U.S. Pat. No. 4,206,206. The cultivation conditions, the nutrient culture medium, the method of isolating the above substance, etc. used for the formation of the antibiotic KA-6606-containing substance are also described in U.S. Pat. No. 4,206,206.

An example of the antibiotic KA-6606-producing strain which can be used in this invention is *Saccharopolyspora hirsuta* KC-6606 strain. This strain is deposited as ATCC 20501 in American Type Culture Collection, U.S.A. and DSM 1238 in German Collection of Microorganisms, West Germany and can be obtained from these depositories. This strain is also deposited as FERM-P No. 3912 in Fermentation Research Institute, Agency of Industrial Science and Technology, Japan. The morphological properties, cultural properties on various media, physiological properties, utilization of carbon sources, etc. of the known strain are disclosed in detail, for example, in U.S. Pat. No. 4,206,206 cited above.

The *Saccharopolyspora hirsuta* KC-6606 strain exemplified above is considered to be a natural mutant of Saccharopolyspora in view of the results of analysis of its various properties mentioned above. The characteristics of the *Saccharopolyspora hirsuta* strain used in this invention readily change, and this strain can be mutated easily by an artificial mutating means using ultraviolet rays, X-rays, various chemicals such as nitrosoguanidines or mitomycin, etc. All such mutants which have the ability to produce the antibiotic KA-6606 substance can be used in this invention.

Suitable nutrient culture media for use in fermenting the KA-6606 substance-producing strain of the genus Saccharopolyspora comprise carbon and nitrogen sources and as optional ingredients, inorganic salts (minerals), very small amounts of heavy metals, etc.

Various carbon sources can be used, and examples of preferred carbon sources are starch, glycerol, maltose, dextrin, sucrose, fructose and molasses, which can be used either alone or as suitable mixtures. Hydrocarbons, organic acids and vegetable oils can also be used if the particular strain can utilize them as a carbon source. Examples of nitrogen sources are soybean meal, yeast extract, dried yeast, peptone, meat extract, corn steep liquor, Casamino acid, Distiller's soluble, ammonium chloride, ammonium sulfate, urea and sodium nitrate, which can be used either alone or as suitable mixtures. Examples of inorganic salts include sodium chloride, potassium phosphate, magnesium sulfate, calcium chloride, calcium carbonate, calcium hydroxide, cobaltous chloride, zinc sulfate, ferric chloride, and ferrous sulfate.

Inorganic substances and organic substances (e.g., amino acids) which aid in the growth of the strain and promote the production of KA-6606 substance can also be added to the culture medium as required. When an aerating cultivation method is employed, an antifoamer such as fatty acid oils, silicone oils and paraffins can also be added to the culture medium.

Cultivation may be carried out in a solid medium. Preferably, however, as in the general process for producing antibiotics, a liquid cultivating method, especially a submerged cultivation method, is used. The cultivation is carried out under aerobic conditions, and the cultivation temperature is generally about 20° to about 40° C., preferably about 27° C. Preferably, during the cultivation, the pH of the culture medium is maintained at about 4 to about 10. The cultivation period is generally about 2 days to about 10 days.

As a result of the cultivation, the KA-6606-containing substance is produced and accumulated in the culture broth. When the amount of the KA-6606-containing substance produced in the culture broth reaches a maximum, the cultivation is stopped, and the KA-6606-containing substance can be collected from the culture broth.

Since the KA-6606-containing substance is a water-soluble basic substance soluble in water but only slightly soluble in common organic solvents, it can be separated from the culture broth by utilizing means which are customarily used in isolating and purifying water-soluble basic antibiotics. For example, there can be used an adsorption-desorption method using an ion exchange resin, active carbon, cellulose, silica gel, alumina, and a method for extracting with butanol, amyl alcohol, etc. using a higher fatty acid as an adjuvant.

For example, if the culture broth filtrate is charged on a column of a weakly acidic cation exchange resin, the KA-6606-containing substance is adsorbed to it. The KA-6606-containing substance is then isolated by elution with a 0.1-3.0N alkali or acid or various salt solutions. The resulting active eluate is lyophilized to afford a crude powder of KA-6606-containing substance.

Examples of the weakly acidic cation exchange resin used to recover the KA-6606-containing substance are Amberlite IRC-50, IRC-84 and CG-50 (tradename: Rohm & Haas Co.); and Diaion WK-10 and WK-20 (tradename: Mitsubishi Chemical Co., Ltd.). Alkalies that can be used for the elution are aqueous ammonia and an aqueous solution of sodium hydroxide. Examples of the acids are formic acid, hydrochloric acid and sulfuric acid. The salt solutions may, for example, include a solution of ammonium carbonate and a solution of ammonium formate. Another example of the recovering method comprises adjusting the pH of the culture broth filtrate to 7 to 9, contacting the filtrate with active carbon to cause the KA-6606-containing substance to be adsorbed to the active carbon, and eluting the substance with acidic water or hydrochloric acid-methanol.

The KA-6606-containing substance that can be isolated by the methods described above can be separated into KA-6606 VII, KA-6606 VIII, KA-6606 IX, KA-6606 X, KA-6606 XI, KA-6606 XII, KA-6606 XIII, KA-6606 XIV, KA-6606 XV, KA-6606 XVI and KA-6606 XVII by dissolving it in water, charging it on a column of an adsorbent such as a weakly acidic ion exchange resin of the type described above or a weakly acidic ion exchanger such as CM-Sephadex (tradename: Pharmacia Co.) or CM Cellulose to cause the substance to be adsorbed to the adsorbent, and then eluting the column by a gradient method beween water and 0.5N aqueous ammonia. According to one embodiment of this separating procedure, crude KA-6606 XII is obtained as the first eluate, and then crude KA-6606 IV, III and I are separated as the second eluate. Subsequently, crude KA-6606 VII is separated. Then, KA-6606 VI and KA-6606 XIII to XVII are obtained as a further eluate. Subsequently, KA-6606 VIII and KA-6606 IX are separated as an eluate. Separation of this eluate into KA-6606 VIII and KA-6606 IX can be effected by charging the eluate on a column of silica gel, and then developing the column with a lower layer of chloroform-methanol-17% aqueous ammonia (2:1:1), for example. Further, KA-6606 II and KA-6606 V are separated as an eluate, and subsequently KA-6606 X is obtained as a further eluate. A subsequent eluate obtained contains KA-6606 XI.

The antibiotics KA-6606 VI and KA-6606 XIII to XVII can be separated from each other by causing a crude powder containing these substances to be adsorbed onto a column of silica gel, and developing the column with, for example, a lower layer of chloroform-methanol-17% aqueous ammonia (2:1:1).

According to the process of this invention, at least one antibiotic selected from the group consisting of antibiotics KA-6606 VII, KA-6606 VIII, KA-6606 IX, KA-6606 X, KA-6606 XI, KA-6606 XII, KA-6606 XIII, KA-6606 XIV, KA-6606 XV, KA-6606 XVI and KA-6606 XVII can be separated and recovered from the KA-6606-containing substance in the above manner.

Each of the antibiotics KA-6606 VII to KA-6606 XVII can be purified by chromatography on cellulose, silica gel, Sephadex (e.g. LH 20), etc. For example, it can be chromatographed on a silica gel column using a lower layer of chloroform-methanol-17% aqueous ammonia (2:1:1) as an eluent.

The antibiotics KA-6606 VII to KA-6606 XVII that can be separated by the method described above are in the form of free bases, and as desired, may be obtained in the form of a pure free base by causing them to be adsorbed to a column of a strongly basic anion exchange resin such as Dowex 1×2 (tradename: Dow Chemical), eluting them with deionized water, collecting active fractions, and lyophilizing the collected fractions.

These KA-6606 VII to KA-6606 XVII obtained as free bases can be converted to their acid addition salts by treatment with pharmaceutically acceptable inorganic or organic acids. Examples of such acids are inorganic acids such as sulfuric acid, hydrochloric acid, hydrobromic acid, hydroiodic acid, phosphoric acid, carbonic acid and nitric acid and organic acids such as acetic acid, fumaric acid, malic acid, citric acid, mandelic acid and succinic acid.

The antibiotics KA-6606 VII to KA-6606 XVII which can be obtained by the process of this invention are basic water-soluble white substances which are useful antibiotics showing antibacterial activity mainly against Gram-positive and Gram-negative bacteria.

Tables 1 and 2 show the antibacterial spectra of the antibiotics KA-6606 VII to KA-6606 XVII against various bacteria, determined by the disc plate method, in comparison with the KA-6606 II substance. Each of the chemicals is used as impregnated in a paper disc having a diameter of 8 mm.

TABLE 1

| Test Bacteria | Inhibition zone (diameter in mm) KA-6606 | | |
|---|---|---|---|
| | II (1 mg/ml) | VII (1 mg/ml) | VIII (1 mg/ml) |
| Staphylococcus aureus 209P | 11.8 | 9.3 | 13.5 |
| Bacillus subtilis ATCC 6633 | 21.0 | 17.8 | 26.2 |
| Escherichia coli NIHJ | 19.0 | 17.5 | 21.9 |
| Proteus vulgaria | 20.8 | 20.1 | 23.3 |
| Proteus inconstans | 13.8 | 9.0 | 18.9 |
| Klebsiella pneumoniae | 15.1 | 9.0 | 18.8 |
| Pseudomonas aeruginosa | 9.2 | — | 17.3 |
| Serratia marcescens | 18.1 | 15.1 | 19.7 |

TABLE 2

| Test bacteria | Inhibition zone (diameter in mm) KA-6606 | | | | | | | | | |
|---|---|---|---|---|---|---|---|---|---|---|
| | II (1 mg/ml) | IX (1 mg/ml) | X (1 mg/ml) | XI (1 mg/ml) | XII (10 mg/ml) | XIII (1 mg/ml) | XIV (1 mg/ml) | XV (1 mg/ml) | XVI (1 mg/ml) | XVII (10 mg/ml) |
| Staphylococcus aureus 209D-JC-1 | 23.8 | 22.9 | 23.3 | 25.2 | 16.8 | 22.0 | 17.1 | 23.3 | 16.3 | 14.2 |
| Bacillus subtilis ATCC 6633 | 22.6 | 23.8 | 22.5 | 23.5 | 17.7 | 22.6 | 19.1 | 23.1 | 20.6 | 17.3 |
| Escherichia coli NIHJ JC-2 | 17.0 | 16.7 | 16.3 | 18.0 | 9.2 | 18.4 | 11.8 | 18.5 | 16.2 | 10.7 |
| Proteus vulgaris OX-107 | 15.7 | 15.2 | 16.6 | 15.1 | 9.3 | 18.5 | 12.0 | 16.4 | 15.8 | 16.8 |
| Proteus inconstans | 16.5 | 9.4 | 11.9 | 19.0 | — | 14.3 | 8.5 | 9.0 | 8.9 | — |
| Klebsiella pneumoniae PCI 602 | 15.8 | 13.7 | 17.4 | 18.5 | — | 17.0 | 9.5 | 18.6 | 8.5 | — |
| Pseudomonas aeruginosa NCTC 10490 | 14.1 | 15.9 | 13.8 | 16.6 | 9.3 | 14.8 | 9.2 | 16.2 | 11.8 | 10.1 |
| Serratia marcescens NHL | 16.6 | 16.0 | 16.5 | 16.8 | 9.8 | 18.5 | 13.5 | 18.2 | 16.3 | 13.6 |

Table 3 shows the Rf values, determined by paper chromatography, of the antibiotics KA-6606 VII to KA-6606 XVII obtained by the process of this invention, KA-6606 I to KA-6606 VI, and known antibiotics.

Developing solvent: a lower layer of chloroform-methanol-17% aqueous ammonia (2:1:1)
Filter paper: Whatmann No. 1

TABLE 3

| Antibiotics | Rf value |
|---|---|
| KA-6606 VII | 0.88 |
| KA-6606 VIII | 0.90 |
| KA-6606 IX | 0.44 |
| KA-6606 X | 0.68 |
| KA-6606 XI | 0.36 |
| KA-6606 XII | 0.00 |
| KA-6606 XIII | 0.97 |
| KA-6606 XIV | 0.95 |
| KA-6606 XV | 0.83 |
| KA-6606 XVI | 0.47 |
| KA-6606 XVII | 0.51 |
| KA-6606 I | 0.53 |
| KA-6606 II | 0.86 |
| KA-6606 III | 0.27 |
| KA-6606 IV | 0.55 |
| KA-6606 V | 0.91 |
| KA-6606 VI | 0.94 |
| Gentamicin $C_1$ | 0.59 |
| Gentamicin $C_2$ | 0.35 |
| Gentamicin $C_{1a}$ | 0.12 |
| Sagamicin | 0.49 |
| Sisomicin | 0.12 |
| Verdamicin | 0.35 |
| G-52 | 0.49 |

TABLE 3-continued

| Antibiotics | Rf value |
|---|---|
| Fortimicin A | 0.32 |
| Fortimicin B | 0.89 |
| Others (*1) | 0.0–0.05 |

(*1): Others represent Kanamycin A, B, C, Paromomycin, Neomycin A, B and C, Butirosine A and B, Lividomycin A and B, Ribostamycin, Xylostatin, Gentamicin A and B, Tobramycin, Apramycin, Sorbicitin, antibiotic substance 460, Hygromycin, or Destomycin.

Table 4 shows the Rf values, determined by thin-layer chromatography, of the antibiotics KA-6606 VII to KA-6606 XVII obtained by the process of this invention, KA-6606 I to KA-6606 VI and known antibiotics.

Developing solvent: (a) butanol-ethanol-chloroform-17% aqueous ammonia (4:5:2:5); (b) chloroform-methanol-17% aqueous ammonia (1:8:3)
Plate: TLC aluminum sheet silica gel 60 $F_{254}$ 0.2 mm (Merck Co.)

TABLE 4

| Antibiotics | Rf value | |
|---|---|---|
| | Solvent (a) | Solvent (b) |
| KA-6606 VII | 0.63 | 0.65 |
| KA-6606 VIII | 0.65 | 0.68 |
| KA-6606 IX | 0.50 | 0.50 |
| KA-6606 X | 0.47 | 0.43 |
| KA-6606 XI | 0.37 | 0.30 |
| KA-6606 XII | 0.23 | 0.37 |
| KA-6606 XIII | 0.62 | 0.64 |
| KA-6606 XIV | 0.60 | 0.67 |
| KA-6606 XV | 0.57 | 0.59 |
| KA-6606 XVI | 0.55 | 0.55 |
| KA-6606 XVII | 0.56 | 0.60 |
| KA-6606 I | 0.56 | 0.60 |
| KA-6606 II | 0.57 | 0.52 |
| KA-6606 III | 0.55 | 0.64 |
| KA-6606 IV | 0.56 | 0.66 |
| KA-6606 V | 0.64 | 0.61 |
| KA-6606 VI | 0.69 | 0.73 |
| Gentamicin $C_1$ | 0.52 | 0.40 |
| Gentamicin $C_2$ | 0.51 | 0.44 |
| Gentamicin $C_{1a}$ | 0.43 | 0.34 |
| Sagamicin | 0.45 | 0.32 |
| Fortimicin A | 0.53 | 0.56 |
| Fortimicin B | 0.60 | 0.70 |

Other physicochemical properties of the antibiotics KA-6606 VII to KA-6606 XVII are summarized in Table 5.

FIGS. 1–11, referred to in Table 5, are charts of the infrared absorption spectra, in potassium bromide, of the antibiotics KA-6606 VII to KA-6606 XVII.

TABLE 5

Figure 2:
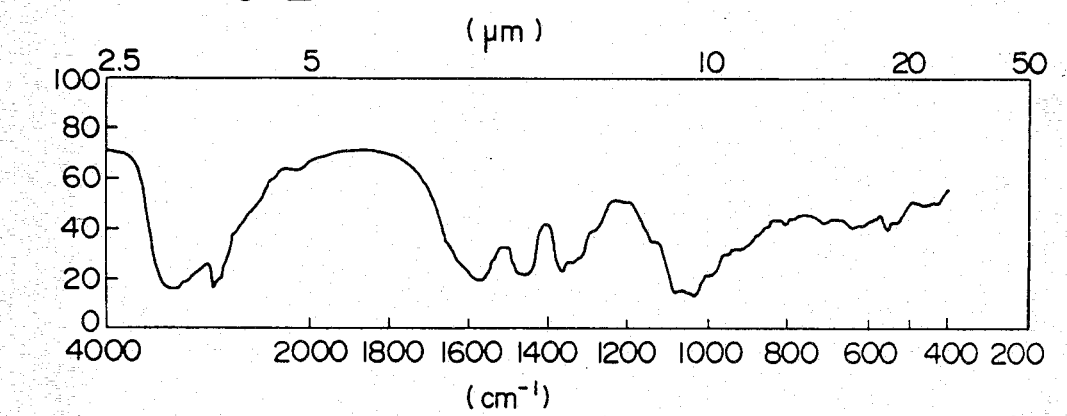
Figure 3:
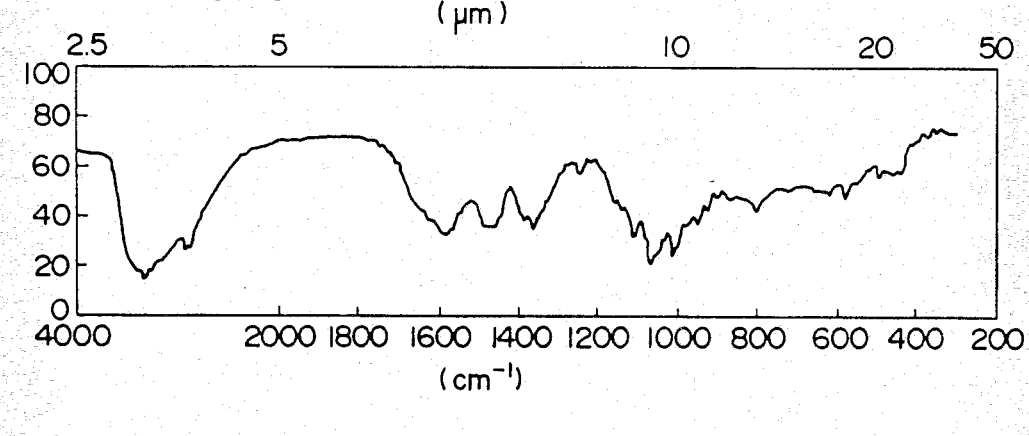
Figure 4:
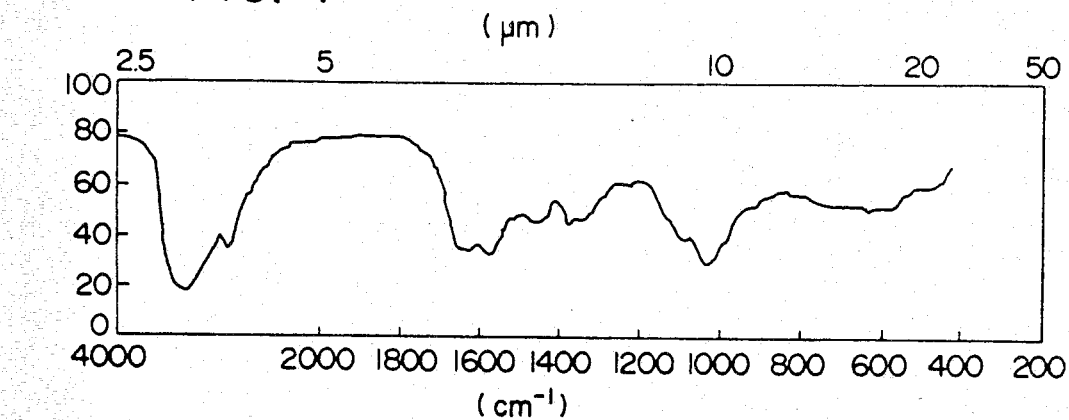
Figure 5:
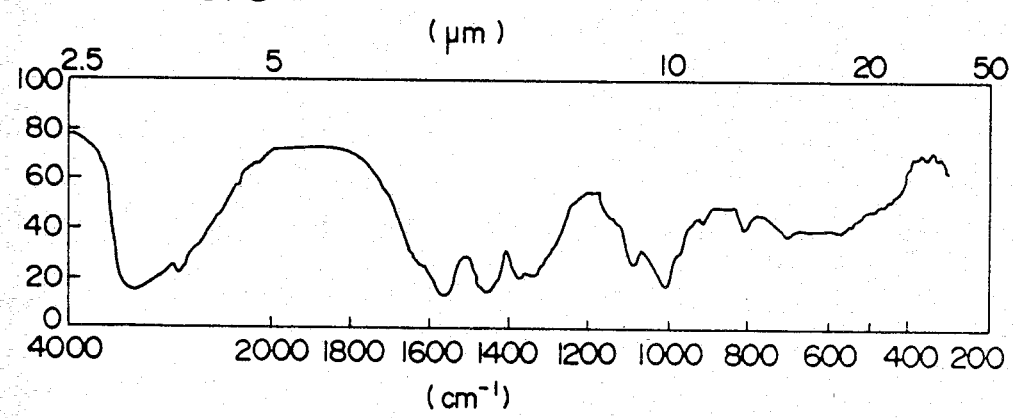
Figure 6:
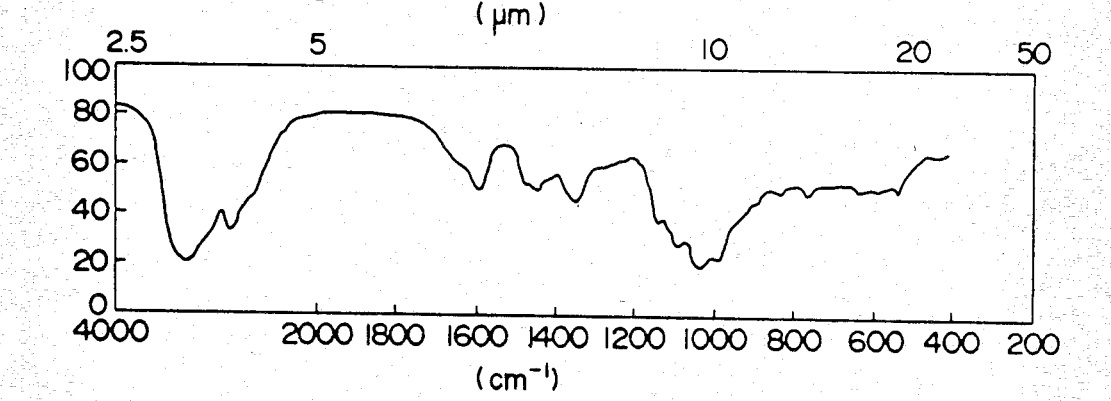

| | | KA-6606 VII | KA-6606 VIII | KA-6606 IX | KA-6606 X | KA-6606 XI | KA-6606 XII |
|---|---|---|---|---|---|---|---|
| Appearance | | White powder | White powder | White powder | White powder | White powder | White powder |
| Molecular formula | | $C_{15}H_{32}O_4N_4$ | $C_{15}H_{32}O_4N_4$ | $C_{14}H_{20}O_4N_4$ | $C_{14}H_{30}O_4N_4$ | $C_{14}H_{30}O_4N_4$ | $C_{13}H_{27}O_7N_3$ |
| Elemental analysis | | | | | | | |
| Calculated | C | 54.19 | 54.19 | 47.36 | 49.98 | 47.36 | 43.93 |
| | H | 9.70 | 9.70 | 8.48 | 9.59 | 8.48 | 8.22 |
| | N | 16.85 | 16.85 | 14.73 | 16.65 | 14.73 | 11.82 |
| | | | | (as mono-carbonate) | (as mono-hydrate) | (as mono-carbonate) | (as mono-hydrate) |
| Found | C | 54.31 | 54.40 | 47.18 | 49.55 | 46.99 | 44.18 |
| | H | 9.92 | 9.78 | 8.25 | 9.62 | 8.52 | 8.37 |
| | N | 16.75 | 16.69 | 14.51 | 16.28 | 14.55 | 11.51 |
| Molecular weight (mass spectrum) | | 332 | 332 | 318 | 318 | 318 | 337 |
| Specific rotation | | $[\alpha]_D^{21} + 78°$ (c 0.4, $H_2O$) | $[\alpha]_D^{21} + 88°$ (c 0.2, $H_2O$) | $[\alpha]_D^{25} + 86°$ (c 1, $H_2O$) | $[\alpha]_D^{25} + 35°$ (c 0.3, $H_2O$) | $[\alpha]_D^{25} + 140°$ (c 2, $H_2O$) | $[\alpha]_D^{25} + 96°$ (c 1, $H_2O$) |
| UV spectrum | | end absorption | end absorption | end absorption | end absorption | end absorption | end absorption |
| IR spectrum (KBr) | | Shown in FIG. 1 | Shown in FIG. 2 | Shown in FIG. 3 | Shown in FIG. 4 | Shown in FIG. 5 | Shown in FIG. 6 |
| Solubility in solvents | | | | | | | |
| Easily soluble | | Water, methanol | Water, methanol | Water, methanol | Water, methanol | Water, methanol | Water, |
| Insoluble | | Ethyl acetate, chloroform | Ethyl acetate, chloroform | Ethyl acetate, chloroform | Ethyl acetate, chloroform | Ethyl acetate, chloroform | Ethyl acetate, chloroform |
| Color reactions | | | | | | | |
| Ninhydrin reaction | | + | + | + | + | + | + |
| Rydone-Smith reaction | | + | + | + | + | + | + |
| Stability | | Stable at pH 2–10 | Stable at pH 2–10 | Stable at pH 2–10 | Stable at pH 2–10 | Stable at pH 2–10 | Stable at pH 2–10 |
| Mass spectrum (m/z) | | 333, 332, 219, 191, 173, 143 | 333, 332, 219, 191, 173, 143 | 318, 205, 177, 159, 143 | 318, 205, 177, 159, 143 | 319 (M + 1), 205, 177, 159, 143 | 328 (M + 1), 205, 177, 162, 159 |
| NMR spectrum ($\delta$, $D_2O$ ppm) | | | | | | | |
| C—$CH_3$ | | 1.48 (d, J = 6.8Hz) | 1.55 (d, J = 6.5Hz) | 1.51 (d, J = 6.5Hz) | 1.56 (d, J = 6.5Hz) | 1.54 (d, J = 6.5Hz) | |
| N—$CH_3$ | | 2.86 (s) | 2.96 (s) | 2.92 (s) | 2.89 (s) | 2.88 (s) | 2.94 (s) |
| O—$CH_3$ | | 3.87 (s) | 3.91 (s) | — | — | — | — |
| Anomelic H | | 5.61 (d, J = 4.2Hz) | 5.61 (d, J = 3.8Hz) | 5.63 (d, J = 3.5Hz) | 5.69 (d, J = 3.5Hz) | 5.46 (d, J = 3,3Hz) | 5.75 (d, J = 3.5Hz) |

Figure 7:
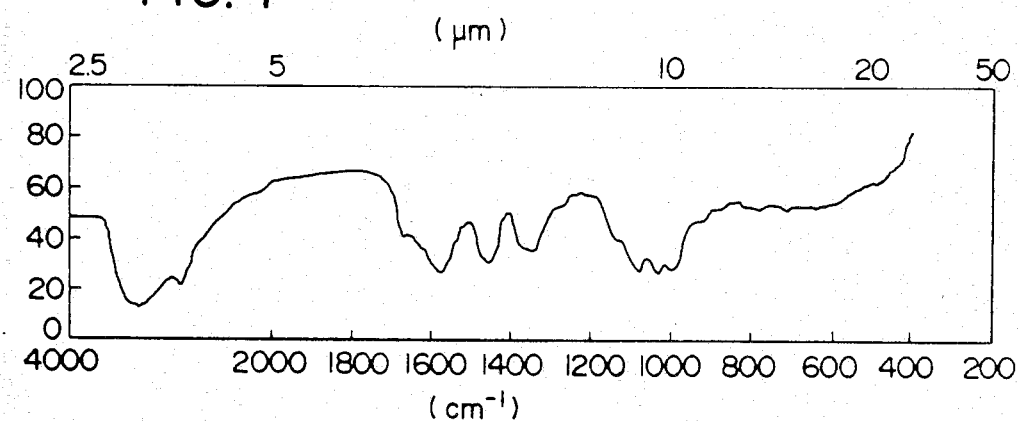
Figure 8:
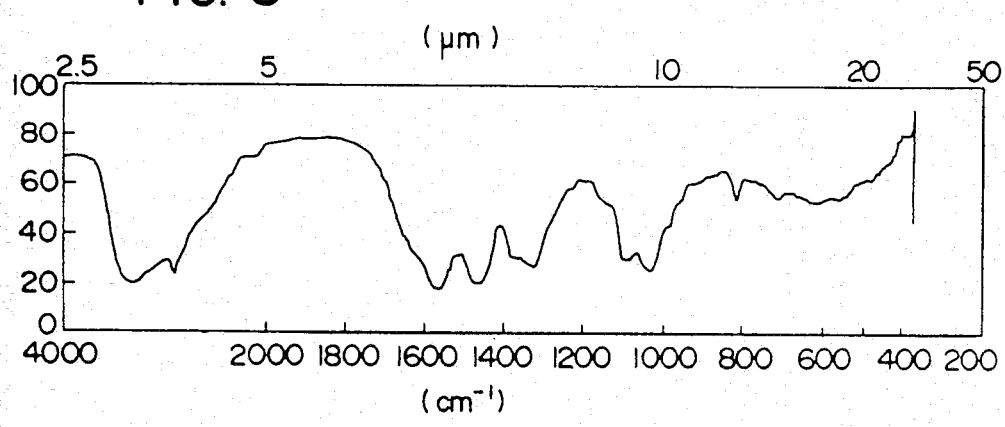
Figure 9:
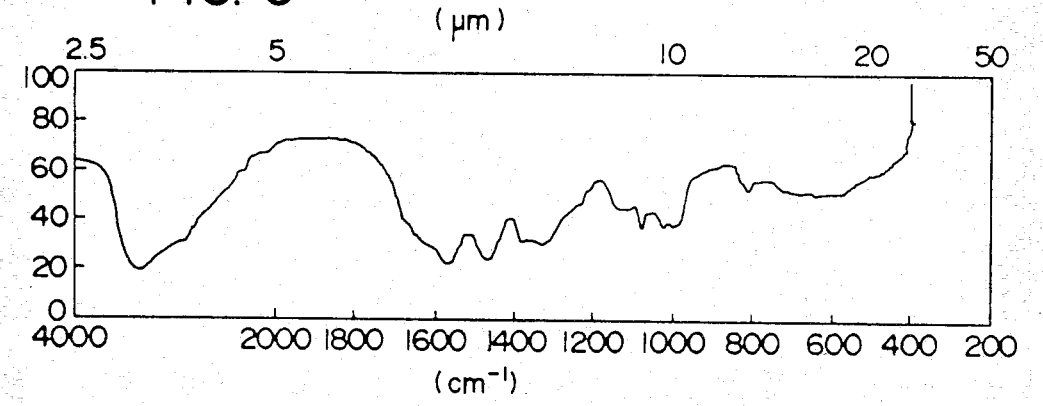
Figure 10:
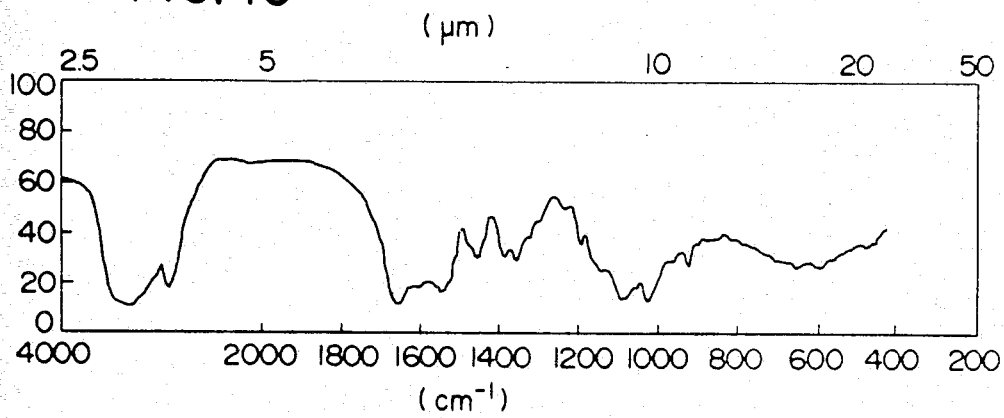
Figure 11:
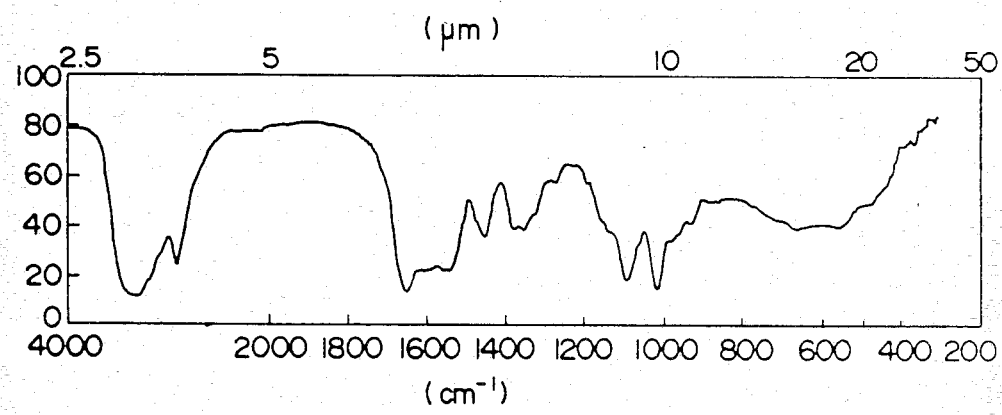

| | | KA-6606 XIII | KA-6606 XIV | KA-6606 XV | KA-6606 XVI | KA-6606 XVII |
|---|---|---|---|---|---|---|
| Appearance | | White powder | White powder | White powder | White powder | White powder |
| Molecular formula | | $C_{15}H_{30}O_4N_4$ | $C_{14}H_{30}O_4N_4$ | $C_{14}H_{28}O_4N_4$ | $C_{16}H_{33}O_5N_5$ | $C_{16}H_{33}O_5N_5$ |
| Elemental analysis | | | | | | |
| Calculated | C | 48.96 | 47.36 | 47.61 | 48.84 | 48.84 |
| | H | 8.22 | 8.48 | 7.99 | 8.97 | 8.97 |
| | N | 14.27 | 14.73 | 14.81 | 17.80 | 17.80 |
| | | (as mono-carbonate) | (as mono-carbonate) | (as mono-carbonate) | (as mono-hydrate) | (as mono-hydrate) |
| Found | C | 48.58 | 47.18 | 47.55 | 48.58 | 48.66 |
| | H | 8.03 | 8.55 | 8.11 | 8.91 | 8.59 |
| | N | 13.95 | 14.48 | 14.46 | 17.32 | 17.61 |
| Molecular weight (mass spectrum) | | 330 | 318 | 316 | 375 | 375 |
| Specific rotation | | $[\alpha]_D^{23} + 138°$ (c 1, $H_2O$) | $[\alpha]_D^{24} + 74°$ (c 0.4, $H_2O$) | $[\alpha]_D^{24} + 126°$ (c 1, $H_2O$) | $[\alpha]_D^{24} + 157.5°$ (c 0.4, $H_2O$) | $[\alpha]_D^{24} + 131.3°$ (c 0.4, $H_2O$) |
| UV spectrum | | end absorption | end absorption | end absorption | end absorption | end absorption |
| IR spectrum (KBr) | | Shown in FIG. 7 | Shown in FIG. 8 | Shown in FIG. 9 | Shown in FIG. 10 | Shown in FIG. 11 |
| Solubility in solvents | | | | | | |
| Easily soluble | | Water, methanol | Water, methanol | Water, methanol | Water, methanol | Water, methanol |
| Insoluble | | Ethyl acetate, chloroform | Ethyl acetate, chloroform | Ethyl acetate, chloroform | Ethyl acetate, choloroform | Ethyl acetate, choloroform |
| Color reactions | | | | | | |
| Ninhydrin reaction | | + | + | + | + | + |
| Rydone-Smith reaction | | + | + | + | + | + |

TABLE 5-continued

| Stability | Stable at pH 2-10 | Stable at pH 2-10 | Stable at pH 2-10 | Stable at pH 2-10 | Stable at pH 2-10 |
|---|---|---|---|---|---|
| Mass spectrum (m/z) | 331, 330, 219, 191, 173 | 318, 219, 191, 173, 129 | 317, 316, 219, 191, 173, 127 | 376, 375, 191, 186, 173 | 376, 375, 262, 234, 143 |
| NMR spectrum ($\delta$, $D_2O$ ppm) | | | | | |
| C—$CH_3$ | 1.66 (d, J = 6.7Hz) | — | | 1.50 (d, J = 6.5Hz) | 1.53 (d, J = 6.5Hz) |
| N—$CH_3$ | 2.84 (s) | 2.83 (s) | 2.91 (s) | 2.80 (s) | 2.85 (s) |
| O—$CH_3$ | 3.83 (s) | 3.87 (s) | 3.85 (s) | 3.88 (s) | 3.90 (s) |
| Anomeric H | 5.78 (d, J = 2.5Hz) | 5.50 (d, J = 3.7Hz) | 5.81 (d, J = 2.3Hz) | 5.49 (d, J = 3.3Hz) | 5.42 (d, J = 3Hz) |

Because of their broad, excellent antimicrobial spectrum as shown in Tables 1 and 2, the antibiotics KA-6606 VII to KA-6606 XVII which can be obtained by the process of this invention are useful as medicines for man and other animals such as poultry, domestic animals and cultivated fish, as antibacterial agents, and also as fungicides against pathogenic fungi on plants. For this purpose, the antibiotics KA-6606 VII to KA-6606 XVII can be used either singly or as a mixture of two or more of them, or a mixture of at least one of these antibiotics with at least one of antibiotics KA-6606 I to KA-6606 VI can be used. The substances obtained by the invention can also be used as starting materials for synthesizing various derivatives.

Thus, according to this invention, there can also be provided an antibiotic composition comprising (1) an antibiotically effective amount of at least one compound selected from the group consisting of KA-6606 VII to KA-6606 XVII substances obtained by the process of this invention and a pharmaceutically acceptable acid addition salt thereof, and (2) a pharmaceutically acceptable diluent or carrier.

The amount of the compound (1) is, for example, about 0.01 to about 99.5% by weight, based on the weight of the composition.

The antibiotic composition may be in any dosage forms usually employed, but injecting preparations and capsules are especially preferred.

Preferably, like known water-soluble basic antibiotics, an injectable is prepared by filling a lyophilized powder of the antibiotic into a vial, preferably together with a stabilizer, and in use, the contents of the vial are dissolved in a dissolving liquid for administration.

The diluent or carrier includes, for example, liquid diluents such as distilled water for injection and physiological isotonic solution, and solid carriers such as lactose, starch, white sugar, glucose, crystalline cellulose, calcium carbonate, kaolin, D-mannitol, magnesium metasilicate aluminate, calcium sulfate, calcium phosphate and bentonite. Addition of stabilizers such as acidic sodium bisulfite is also preferred.

The dosage of the antibiotic substance of this invention can be suitably selected, and is, for example, about 0.01 to about 100 mg/kg/day.

The following Example illustrates the present invention more specifically.

EXAMPLE

*Saccharopolyspora hirsuta* KC-6606 strain was inoculated in a sterilized culture medium adjusted to pH 7.2 and containing 4% of starch, 1.8% of soybean meal, 0.1% of yeast extract, 0.4% of corn steep liquor, 0.3% of sodium chloride, 0.05% of magnesium sulfate heptahydrate, 0.03% of calcium chloride, and 0.005% of cobaltous chloride hexahydrate, and cultivated at 30° C. for 2 days to form a first seed culture. A 20-liter jar fermentor was charged with 10 liters of a culture medium obtained by adding 2.0% of cotton seed oil to the same culture medium as used in forming the first seed culture, and 200 ml of the first seed culture was inoculated in the culture medium and cultivated at 30° C. for 2 days by an aeration-stirring method (240 rpm; the air flow rate 10 liters/min.) to form a second seed culture. A 5000-liter fermentor was charged with 2500 liters of a culture medium having the same composition as the culture medium used in forming the second seed culture. Ten liters of the second seed culture was inoculated in the culture medium, and cultivated at 30° C. for 7 days by an aeration-stirring method (120 rpm; the air flow rate 2500 liters/min.).

After the cultivation, sulfuric acid was added to the culture broth to adjust its pH to 2.0, and Celite (a product made by Johns-Manville Products Corporation) was added as a filter aid. The culture broth was thus filtered to remove the microbial cells. A 48% aqueous solution of sodium hydroxide was added to the filtrate to adjust its pH to 7.0. The filtrate was then passed through a column (20×150 cm) of a cation exchange resin (Amberlite IRC-50, $NH_4^+$ form) to cause adsorption of active substances thereto. The column was then washed with water, and eluted with 1N aqueous ammonia. Active portions were collected, concentrated under reduced pressure, and lyophilized to give 200 g of a crude KA-6606 substance powder.

This crude powder (200 g) was dissolved in 20 liters of distilled water, and the pH of the solution was adjusted to 7.0 with dilute sulfuric acid. The solution was then passed through a column (10×400 cm) of a cation exchange resin (CM-Sephadex C-25, $NH_4^+$ form). The column was washed with water, and then eluted by a concentration gradient method between 250 liters of water and 250 liters of 0.5N aqueous ammonia. The eluates were fractionated into 5-liter fractions, and each of the fractions was examined for activity by the paper disc method using an agar plate of *Bacillus subtilis*. The composition of each fraction was further examined by thin-layer chromatography.

In the first place, a fraction containing KA-6606 XII was obtained, and then fractions containing KA-6606 IV, III and I, respectively, and a fraction containing KA-6606 VII were successively obtained. When the elution was further continued, a fraction containing a mixture of KA-6606 VI and XIII to XVII, a fraction containing a mixture of KA-6606 VIII and IX, a fraction containing KA-6606 II and a fraction containing KA-6606 V were successively obtained. Further, a fraction containing KA-6606 X was obtained followed by elution of KA-6606 XI. When these fractions were lyophilized, there were obtained 112 mg of a crude powder of KA-6606 XII, 100 mg of a crude powder of KA-6606 VII, 700 mg of a crude powder composed of KA-6606 VI and XIII to XVII, 109 mg of a crude powder composed of KA-6606 VIII and IX, 109 mg of a crude powder of KA-6606 X and 62 mg of a crude powder of KA-6606 XI, respectively.

112 mg of the crude powder of KA-6606 XII was filled as a uniform layer on a column (1×30 cm) of silica gel, and chromatographed using chloroform-methanol-17% aqueous ammonia (1:8:2). Fractions containing KA-6606 XII substance were collected, concentrated under reduced pressure, and again dissolved in water. The aqueous solution was charged on a column (1×40 cm) of a weakly acidic cation exchange resin (CM-Sephadex C-25, $NH_4^+$ form). The column was then washed with water and eluted by a concentration gradient method between 300 ml of water and 300 ml of 0.2N aqueous ammonia. Fractions containing KA-6606 XII were collected and lyophilized to give 40 mg of a colorless powder of the above substance as a free base.

1000 mg of the crude powder of KA-6606 VII was again dissolved in water, and the solution was charged on a column (1.5×100 cm) of a weakly acidic cation exchange resin (CM-Sephadex C-25, $NH_4^+$ form). The column was washed with water, and eluted by a concentration gradient method between 2 liters of water and 2 liters of 0.4N aqueous ammonia. Fractions containing the KA-6606 VII substance were collected and lyophilized to give 138 mg of a coloress solid of the above substance as a free base.

700 mg of the crude powder containing KA-6606 VI and XIII to XVII was filled as a uniform layer on a column (3×100 cm) of silica gel, and chromatographed using a lower layer of chloroform-methanol-17% aqueous ammonia (2:1:1). The first eluate contained KA-6606 VI; the second eluate contained a mixture of KA-6606 XIII and KA-6606 XIV; the third eluate contained KA-6606 XV; and the fourth eluate contained a mixture of KA-6606 XVII and KA-6606 XVI. These eluates were collected, concentrated under reduced pressure, and again dissolved in water. The aqueous solution was charged on a column (1×40 cm) of a weakly acidic cation exchange resin (CM-Sephadex C-25, $NH_4^+$ form). The column was washed with water, and eluted by a concentration gradient method between 300 ml of water and 300 ml of 0.4N aqueous ammonia. From the fraction containing KA-6606 VI, 180 mg of a colorless solid of the above substance as a free base was obtained. From the fraction containing the mixture of KA-6606 XIII and KA-6606 XIV, 11 mg of a colorless solid of KA-6606 XIV as a free base was first eluted and 50 mg of a colorless solid of KA-6606 XIII as a free base was then eluted. From the fraction containing KA-6606 XV, 12 mg of a colorless solid of this substance as a free base was obtained. From the fraction containing the mixture of KA-6606 XVII and KA-6606 XVI, there were obtained 19 mg of a colorless solid of KA-6606 XVII as a free base eluted first and 150 mg of a colorless solid of KA-6606 XVI as a free base eluted next.

109 mg of the crude powder containing KA-6606 VIII and IX was filled as a uniform layer on a column (1.5×50 cm) of silica gel, and chromatographed using a lower layer of chloroform-methanol-17% aqueous ammonia (2:1:1). First, KA-6606 VIII was eluted, and then KA-6606 IX was eluted. The fractions containing each of these substances were collected, concentrated under reduced pressure, and again dissolved in water. The aqueous solution was charged on a column (1×40 cm) of a weakly acidic cation exchange resin (CM-Sephadex C-25, $NH_4^+$ form). The column was washed with water, and then eluted by a concentration gradient method between 300 ml of water and 300 ml of 0.4N aqueous ammonia. The fractions containing KA-6606 VIII were lyophilized to give 15 mg of a colorless solid as a free base. The fractions containing KA-6606 IX were lyophilized to give 52 mg of a colorless powder as a free base.

109 mg of the crude powder of KA-6606 X was again dissolved in water. The aqueous solution was charged on a column (1×40 cm) of a weakly acidic cation exchange resin (CM-Sephadex C-25, $NH_4^+$ form). The column was washed with water, and eluted by a concentration gradient method between 300 ml of water and 300 ml of 0.4N aqueous ammonia. The fractions containing KA-6606 X were collected and lyophilized to give 14 mg of a colorless powder as a free base.

62 mg of the crude powder of KA-6606 XI was again dissolved in water. The aqueous solution was charged on a column (1×40 cm) of a weakly acidic cation exchange resin (CM-Sephadex C-25, $NH_4^+$ form). The column was washed with water and eluted by a concentration gradient method between 300 ml of water and 300 ml of 0.4N aqueous ammonia. The fractions containing KA-6606 XI were collected, and lyophilized to give 4 mg of a colorless powder of this substance as a free base.

The resulting compounds KA-6606 VII to XVII had similar physicochemical properties to those shown in Tables 3 to 5, which supported the structure formulae shown hereinabove.

What we claim is:

1. A substantially pure material which is at least one member selected from the group consisting of antibiotics KA-6606 XII, XIII and XV to XVII of the following formulae

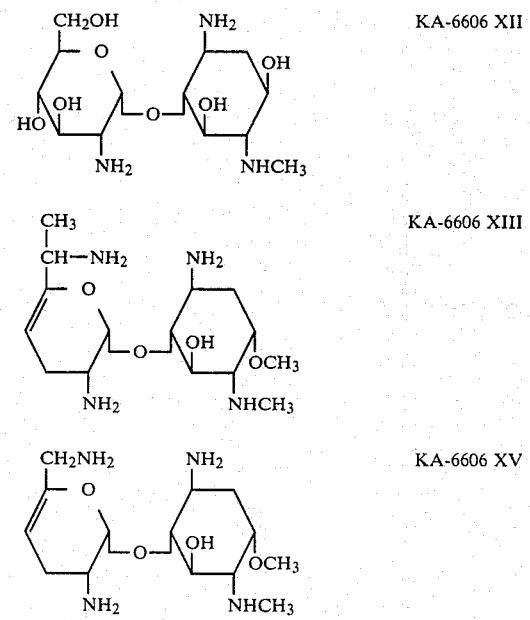

KA-6606 XVI
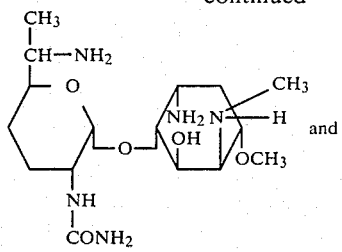
and
KA-6606 XVII
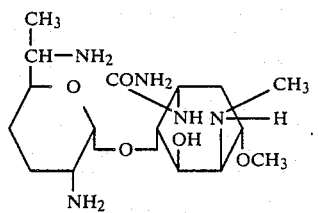
* * * * *